United States Patent
Avramoff et al.

(10) Patent No.: US 10,548,837 B1
(45) Date of Patent: Feb. 4, 2020

(54) TOPICAL MONTELUKAST FOR TREATMENT OF ATOPIC DERMATITIS

(71) Applicant: TARO PHARMACEUTICAL INDUSTRIES LTD., Haifa Bay (IL)

(72) Inventors: Avi Avramoff, Haifa (IL); Helena Shifrin, Rehovot (IL); Irena Oleinik, Karmiel (IL); Ron Schlinger, Tel-Aviv (IL); Tzviel Sheskin, Haifa (IL); Vered Rosenberger, Givatayim (IL)

(73) Assignee: TARO PHARMACEUTICAL INDUSTRIES LTD., Haifa Bay (IL)

( * ) Notice: Subject to any disclaimer, the term of this patent is extended or adjusted under 35 U.S.C. 154(b) by 0 days.

(21) Appl. No.: 15/585,689

(22) Filed: May 3, 2017

Related U.S. Application Data (60) Provisional application No. 62/331,528, filed on May 4, 2016.

(51) Int. Cl.
| | | |
|---|---|---|
| *A61K 31/47* | (2006.01) | |
| *A61K 9/00* | (2006.01) | |
| *A61K 31/495* | (2006.01) | |
| *A61K 45/06* | (2006.01) | |
| *A61K 31/00* | (2006.01) | |

(52) U.S. Cl.
CPC ............ *A61K 9/0014* (2013.01); *A61K 31/47* (2013.01); *A61K 31/495* (2013.01); *A61K 45/06* (2013.01); *A61K 31/00* (2013.01)

(58) Field of Classification Search
CPC ....... A61K 31/47; A61K 45/00; A61K 9/0014
USPC ...................................................... 514/311
See application file for complete search history.

(56) References Cited

U.S. PATENT DOCUMENTS

| | | |
|---|---|---|
| 2011/0124681 A1 | 5/2011 | Schlesinger |
| 2011/0311613 A1 * | 12/2011 | Hutchinson .......... A61K 9/0014 424/450 |

FOREIGN PATENT DOCUMENTS

| | | | |
|---|---|---|---|
| WO | WO 2008105803 A1 * | 9/2008 | ......... A61K 31/4184 |
| WO | WO 2008106081 A1 * | 9/2008 | ............. A61K 31/38 |
| WO | 2010/104281 A2 | 9/2010 | |

OTHER PUBLICATIONS

Mougey et al, Pharmacogenet Genomics (2009), vol. 19(2), pp. 129-138.*

Irena Angelova-Fischer MD, et al.; "Successful treatment of severe atopic dermatitis with cysteinyl leukotriene receptor antagonist montelukast"; Case Report; Acta Dermatoven APA vol. 14, No. 3, pp. 115-119; Date: Sep. 2005.

Graziano Riccioni, et al.; "Brief Review: Advances in Therapy with Antileukotriene Drugs"; the Association of Clinical Scientists, Inc.; Annals of Clinical & Laboratory Science, vol. 34, No. 4, pp. 379-387; Date: 2004.

P. S. Friedmann, et al., A double-blind, placebo-controlled trial of montelukast in adult atopic eczema; Journal compilation; Blackwell Publishing Ltd; Clinical and Experimental Allergy; vol. 37, Issue 10, pp. 1536-1540; Date: 2007.

(Continued)

*Primary Examiner* — Craig D Ricci
*Assistant Examiner* — Janet L. Coppins
(74) *Attorney, Agent, or Firm* — MEDLER FERRO WOODHOUSE & MILLS PLLC (57) ABSTRACT

A topical formulation comprising Montelukast or a pharmaceutically acceptable salt thereof, a gelling agent and water for the treatment of atopic dermatitis.

7 Claims, 7 Drawing Sheets

(56) References Cited

OTHER PUBLICATIONS

J.M. Rackal3, HBSC, MHSC, et al.; "The Treatment of Atopic Dermatitis and Other Dermatoses with Leukotriene Antagonists"; Skin Therapy Letter, Editor: Dr. Stuart Maddin, vol. 9, No. 2, pp. 1-12; Date Feb. 2004.
Gyeong Il Kim, et al., "The Skin Response to Dimethyl Sulfoxide in Normal Persons and Atopy Patients", Korean Dermatological Association; ISSn 0494-4739 Korean Journal of Dermatology; vol. 40; No. 1, pp. 8; Date Jan. 2002.
Steinke, John W. and Culp, Jeffrey A., "Leukotriene Synthesis Inhibitors Versus Antagonists: The Pros and Cons", Current Allergy and Asthma Reports, 2007, 7:126-133.

\* cited by examiner

Fig. 1

Fig. 2A
Disease Control

Fig. 2B
Disease Control

Fig. 2C
Placebo of Montelukast Sodium Gel

Fig. 2D
Montelukast Sodium Gel

Fig. 2E
Placebo of Montelukast sodium cream

Fig. 2F
Montelukast sodium cream

Fig. 2G
Betamethasone Valerate Cream IP

TOPICAL MONTELUKAST FOR TREATMENT OF ATOPIC DERMATITIS

This application claims priority to the U.S. Provisional Patent Application No. 62/331,528 filed on May 4, 2016, the disclosure of which is incorporated by reference herein.

BACKGROUND

Atopic dermatitis is an increasingly common pruritic, chronic, inflammatory skin disorder. There has been a striking rise in the incidence of Atopic dermatitis (AD) during the past two decades, which is not simply due to an increased recognition of the disease. Population studies suggest that in most countries, AD now affects at least 10-20% of children at some point during childhood. In particular, higher prevalence has been recorded in urban regions than in rural regions of development countries, and the disease is more common in higher social class groups, suggesting that environmental factors associated with more industrialized and urban living determine expression of AD.

There are pathogenic mechanisms that are in common to both AD and asthma. The exaggerated inflammatory response (including increased production of IgE and eosinophilia) to environmental triggers, including irritants and allergens is characteristic of both AD and asthma. Total IgE levels are elevated in both AD and asthma. Genetic studies have demonstrated common chromosomal linkages between AD and asthma.

Leukotrienes (LTs) are a class of potent biological inflammatory mediators derived from arachidonic acid through the 5-lipoxygenase pathway Leukotrienes are divided into two groups according to their chemical structure: those with a sulphur linkage (cysteinyl LTs: $LTC_4$, $LTD_4$, $LTE_4$), and those that lack one ($LTB_4$). Eosinophils, basophils and mast cells are the most important sources of LTs. Epidermal cells are able to transform neutrophil derived $LTA_4$ into $LTB_4$ and $LTC_4$. Thus the epidermis can also contribute significantly to LT synthesis. It has been shown that cysteinyl leukotrienes (cysLTs) mediate asthma and allergic rhinitis and when the LT receptors are antagonized, symptoms resolve. Leukotrienes are important pro inflammatory mediators that are capable of inducing airway smooth muscle constriction, airway hyper responsiveness, eosinophil migration, vascular permeability, edema, and chemotaxis. A role for LTs in AD has been suggested in the literature. There is evidence of enhanced LT production in the pathogenesis of AD. The cysteinyl LTs increase vascular permeability and dilate skin blood vessels. $LTC_4$ has been found in the skin of AD patients using the suction blister technique. Patients with AD have activated circulating basophils and increased basophil releasability of $LTC_4$. Cysteinyl LT release from basophils and cosinophils isolated from AD patients is increased compared to healthy controls. Enhanced spontaneous and stimulated release ability of $LTC_4$ from leukocytes of patients with AD compared with normal controls has been reported. Increased production of LTs has been reported in the skin of atopic patients after allergen specific challenge.

There are at least two types of LT receptors: cysLT1 and cysLT2. Montelukast (Singulair®, Merk-Frosst), zafirlukast (Accolate®, Zeneca), and pranlukast (Ultair®, SmithKline Beecham) are LT receptor antagonists that demonstrate high-affinity binding to the cysLT1 receptor. Montelukast is currently indicated for the prophylaxis and chronic treatment of asthma in adults and pediatric patients 12 months of age and older and for the relief of symptoms of seasonal allergic rhinitis in adults and pediatric patients 2 years of age and older. Montelukast is generally a safe drug during long term treatment; side effects are minimal. Asthma and allergic rhinitis have numerous pathophysiological elements in common with AD, and together these three diseases are referred to as the "atopic triad". As outlined above there are pathogenic mechanisms that are central to both AD and asthma. Evidence in the literature provides a pathophysiological rationale for the use of cysLT receptor blockers in the treatment of AD however the exact mechanism of action of leukotriene receptor antagonists in AD is not known. Intradermal $LTD_4$ causes a wheal-and-flare response that could be blocked by a $LTD_4$ antagonist. Montelukast has been shown to decrease eosinophils by 15%. $LTD_4$ stimulates proliferation of eosinophil hematopoietic progenitor cells, and this increase can be suppressed by Montelukast.

The major function of the skin is to protect the body against physical and chemical injury and to prevent loss of body water and other substances. The stratum corneum (SC) is the outmost layer of the skin which is being continually replaced. By so doing the skin is well adapted to its requirements for repairing damage from wear and tear. However, in Atopic Dermatitis environmental and individual factors interact in a complex manner to induce skin abnormalities and dryness. Application of moisturizers to the skin induces changes in its superficial as well as deep layers. The chemical and physical characteristics of the individual ingredients of the formulation determine the performance of the drug product.

Moreover, in topical treatments of dermatological conditions the efficacy is likely to depend on the dosage, where compliance is a great challenge faced in the management of the diseases.

Montelukast sodium exerts additional challenge to be formulated in a semi solid formulation even for experienced formulators.

Sodium montelukast (Singulair), chemically known as [sodium 1-(1-(3-(2-(7-chloro-2-quinolinyl)-(E)-ethenyl)-phenyl)(3-(2-(1-hydroxy-1-methylethyl)phenyl)propyl) thio)-methyl)-cyclo-propane) acetate is a photosensitive compound requiring special handling precautions to protect specimens from light especially in a solution.

In the montelukast molecule there are number of functional groups that impair the chemical stability of this substance. Montelukast is known to be prone to the formation of several types of impurities:

1. a sulfoxide impurity: [1-[((RS)[1-[3-[(E)-2-(7-Chloroquinolin-2-yl)ethenyl)phenyl)-3-[2-(1-hydroxy-1-methylethyl)phenyl)propyl] sulfinyl] methyl] cyclopropyl]acetic acid;
2. a diol impurity: 2-(2-(3-(S)-(3 (E)-(2-(7-Chloro-2-quinolinyl)-ethenyl)phenyl)-3-hydroxypropyl)phenyl)-2-propanol;
3. a methyl styrene impurity: [1-[[[(1 R)-1-[3-[(E)-2-(7-Chloroquinolin-2-yl)etheny[ ]phenyl]-3-[2-(1-methylethenyl)phenyl]propyl] sulfanyl]melhyl] cyclopropyl] acetic acid (USP imp F);
4. a cis-isomer impurity: [1-[[[(1 R)-1-[3-[(Z)-2-(7-Chloroquinolin-2-yl)ethenyl]phenyl]-3-[2-(1-hydroxy-1-methylethyl)phenyl]propyl] sulfanyl]methyl] cyclopropyl] acetic acid;
5. a Michael adduct impurity (1): 1-[[((1 R)-1-[3-[(1 R)-1 [[[1-(Carboxymethyl)cyclapropyl]methyl] sulfanyl]-2-(7-chloroquinolin-2-yl)ethyl]phenyl]-3-[2-(1-hydroxy-1-methylethyl)phenyl]propyl]suifanyl]methyl]cyclopropyl-lacetic acid;
6. a Michael adduct impurity (2): 1-[[[(1 R)-1-[3-[(1 S)-1-[[[1-(Carboxymethyi)cyclopropyl]methyl] sulfanyl]-2-

(7-chloroquinolin-2-yl)ethyl]phenyl]-3-[2-(1-hydroxy-1-methylethyl)phenyl]propyl]sulfanyl]methyl]cyclopropyl] acetic acid;

7. a methyl ketone impurity: [1-({((1R)-3-(2-acetylphenyl)-1-[3-[(E)-2-(7-chloroquinolin-2-yl)ethenyl]phenyl]propyl]sulfanyl] methyl] cyclopropyl]acetic acid.

SUMMARY OF THE INVENTION

In one aspect, the present invention provides a topical formulation comprising 1-(1-(3-(2-(7-chloro-2-quinolinyl)-(E)-ethenyl)-phenyl)(3-(2-(1-hydroxy-1-methylethyl)phenyl)propyl) thio)-methyl)-cyclo-propane) acetate (montelukast) or a pharmaceutically acceptable salt thereof, a gelling agent and water for the treatment of atopic dermatitis.

In one aspect, the present invention provides a topical formulation comprising Montelukast or a pharmaceutically acceptable salt thereof and at least one oil for the treatment of atopic dermatitis wherein the formulation is waterless.

BRIEF DESCRIPTION OF THE DRAWINGS

The patent or application file contains at least one drawing executed in color. Copies of this patent or patent application publication with color drawing(s) will be provided by the United States Patent Office upon request and payment of the necessary fee.

DETAILED DESCRIPTION OF THE INVENTION

The present invention relates to a topical formulation comprising Montelukast or a pharmaceutically acceptable salt thereof, a gelling agent and water for the treatment of atopic dermatitis. In certain embodiments the salt is an alkali metal salt, such as sodium or potassium; an alkaline earth salt; or an ammonium salt.

Furthermore, the term "montelukast" as used herein encompasses polymorph crystal forms and any other form of montelukast that has one or more of the pharmaceutical activities of montelukast.

In certain embodiments, the topical formulation may comprise about 0.01% w/w to about 10% w/w montelukast or a pharmaceutically acceptable salt.

In certain embodiments, the concentration of montelukast or a pharmaceutically acceptable salt in the topical formulation is between about 0.5% w/w to about 5% w/w.

In certain embodiments, the concentration of montelukast or a pharmaceutically acceptable salt in the topical formulation is between about 5% w/w to about 10% w/w In preferred embodiments, the concentration of montelukast or a pharmaceutically acceptable salt in the topical formulation is 5% w/w.

In one embodiment of the present invention, the topical formulation of montelukast or a pharmaceutically acceptable salt can be a gel. In one embodiment, a gel may be prepared by providing a gelling agent and adding an excipient such as water in case of a hydrous gel. The gel may include a variety of additional components such as, but not limited to solvents, emulsifiers, thickeners, stabilisers, gelling agents, chelating agents, surfactants, emollients, permeation enhancers, preservatives, antioxidants, lubricants, pH adjusters.

In one embodiment, the topical formulations of Montelukast or a pharmaceutically acceptable salt thereof provide topical penetration of the active agent through the epidermis and into the dermis.

In some embodiments, the topical formulations described above comprise penetration enhancers, which facilitate the penetration of the active agent and preferably dissolve the active ingredient present in the formulations of the invention There are numerous penetration enhancers that can be used in accordance with the present invention. Various useful permeation enhancers include, for example: polyols and esters, including polyethylene glycol, polyethylene glycol monolaurate, and butanediol; sulfoxides, including dimethylsulfoxide and decylmethylsulfoxide; ethers, including diethylene glycol monoethyl ether (e.g., Transcutol® P) and diethylene glycol monomethyl ether; fatty acids, including lauric acid, oleic acid, and valeric acid; fatty acid esters, including isopropyl myristate, isopropyl palmitate, methyl propionate, and ethyl oleate; nitrogenous compounds including urea, dimethyl acetamide, dimethylformamide 2-pyrrolidone, ethanolamine, methyl-2-pyrrolidone, diethanolamine, and triethanolamine; terpenes; alkanones; organic acids, including salicylic acid, citric acid, and succinic acid; and any mixtures thereof. A penetration enhancer can be used in concentrations ranging from about 1-15% by weight, preferably about 2-12% by weight, and more preferably about 3-10% by weight, of the total composition.

In certain embodiments of the invention, the pH of the topical gel formulation of montelukast or a pharmaceutically acceptable salt is less than 6. Typically the pH is in the range from 4 to 6. In a more preferred embodiment, the pH is in the range of 5 to 6.

In one embodiment of the present invention, the topical formulation of montelukast or a pharmaceutically acceptable salt may comprise a gelling agent. Examples of suitable gelling agents for use in the present invention may include, but are not limited to hyaluronic acid and its salts such as Sodium Hyaluronate, cellulose derivatives such as hydroxypropyl cellulose (HPC), Hydroxyethyl cellulose (Natrosol 250 HEC HHX), carbomers such as sodium carbomer.

In one embodiment, suitable topically acceptable solvents may also be used in the topical composition. Suitable topically acceptable solvents for use in the present invention include, but are not limited to lower alcohols, ethanol, isopropanol, benzyl alcohol, propanol, methanol, other C4-C10 mono alcohols and mixtures thereof. In another embodiment, the solvents suitable for use in the formulation of the present invention may include albumin, gelatin, citric acid, ethylenediaminesodiumtetraacetate, dextrin, dimethylsulfoxide, dimethylacetamide, dimethylformamide, 2-pyrrolidone, N-(2-hydroxyethyl) pyrrolidone, N-methylpyrrolidone, 1-dodecylazacycloheptan-2-one and other n-substituted-alkyl-azacycloalkyl-2-ones(azones), sodium hydrosulfite and mixtures thereof. In some embodiments, the topical formulation of the invention comprises a polar aprotic solvent, preferably selected from anyone or more of the following: dimethylsulfoxide, dimethyl acetamide, dimethylformanmide or N-methylpyrrolidone.

In another embodiment of the present invention, the topical formulation of montelukast or a pharmaceutically acceptable salt may further comprise an antioxidant such butylated hydroxy anisole or butylated hydroxy toluene; preservatives such as a paraben which include a methyl paraben or propyl paraben.

In one aspect of the invention, the topical formulation of montelukast or a pharmaceutically acceptable salt may comprise a triglyceride. In a preferred embodiment, if a triglyceride is present, it may be a medium chain triglyceride (MCT) of e.g. hexanoic acid; octanoic acid; decanoic acid or dodecanoic acid.

In certain embodiments, the topical formulation described above comprises an occlusive ingredient, such as petroleum jelly/white petrolatum; a wax; an oil; a silicone; a film forming polymer, such as hyaluronic acid, hydroxypropyl cellulose (HPC) or a poly (meth) acrylate, (e.g. Eudragit®); or any combination thereof, and said formulation is therefore an occlusive formulation.

The pharmaceutically acceptable inactive ingredients of the formulation described above may further comprise an oil, such as castor oil or a castor oil derivative (e.g. trihydroxystearin), fractionated coconut oil, or olive oil; an occlusive ingredient, such as petroleum jelly/white petrolatum, a wax, an oil, a silicone, glycerin; an MCT of e.g. hexanoic acid, octanoic acid, decanoic acid or dodecanoic acid; an antioxidant, such as butylated hydroxyanisole; or any combination thereof.

The topical formulation described above may comprise a colloidal solution/suspension, wherein the active agent is in the form of microparticles that are suspended in said formulation, i.e. particles having a diameter of about 1-100 μm. Alternatively, the topical formulation may comprise a microparticle or nanoparticle comprising or encapsulating the active agent, wherein said microparticle or nanoparticle is selected from the group consisting of (a) a solid lipid nanoparticle; (b) a liposome; and (c) a polymeric microparticle or nanoparticle.

In certain embodiments, the solid lipid nanoparticle comprises a lipid selected from the group consisting of cholesterol, a triglyceride, a phospholipid, a fat and a wax.

In certain embodiments, the solid lipid nanoparticle or liposome comprises a phospholipid selected from the group consisting of a lecithin, such as egg or soybean lecithin; a phosphatidylcholine such as egg phosphatidylcholin; a hydrogenated phosphotidylcholine; a lysophosphatidylcholine; dipalmitoylphosphatidylcholine; distearoylphosphatidylcholine; dimyristoylphosphatidylcholine; dilauroylphosphatidylcholine; a glycerophospholipid such as phosphatidylglycerol, phosphatidylserine, phosphatidylethanolamine, lysophosphatidylethanolamine, phosphatidylinositol, phosphatidylinositol phosphate, phosphatidylinositol bisphosphate and phosphatidylinositol triphosphate; sphingomyelin; cardiolipin; a phosphatidic acid; a glycolipid such as a glyceroglycolipid, e.g. a galactolipid and a sulfolipid, a glycosphingolipid, e.g. a cerebroside (a glucocerebroside and a galactocerebroside), and a glycosylphosphatidylinositol; a plasmalogen; a phosphosphingolipid such as a ceramide phosphorylcholine, a ceramide phosphorylethanolamine and a ceramide phosphorylglycerol; and a mixture thereof.

The phospholipid may further be admixed with one or more nonphosphorous-containing molecules selected from the group consisting of a fatty amine, such as octylamine, laurylamine, N-tetradecylamine, hexadecylamine, stearylamine, oleylamine, tallow amine, hydrogenated tallow amine, and cocoamine; a fatty acid; a fatty acid amide; an ester of a fatty acid such as isopropyl myristate, hexadecyl stearate, and cetyl palmitate; cholesterol; a cholesterol ester; a diacylglycerol; a glycerol ester, such as glycerol ricinoleate; and a mixture thereof.

In certain embodiments, the polymeric microparticle or nanoparticle comprises a polymer selected from the group consisting of a silicone; poly(lactic-co-glycolic acid (PLGA); polylactic acid (PLA); chitosan; gelatine; ethylcellulose; polycaprolactone; a polyalkyl cyanoacrylate; and any combination thereof.

In any one of the topical formulations described above, if a triglyceride is present, it may be a medium chain triglyceride (MCT) of e.g. hexanoic acid; octanoic acid; decanoic acid or dodecanoic acid.

The topical formulations described above provide topical penetration of the active agent through the epidermis and into the dermis.

In some embodiments, the topical formulations described above comprise penetration enhancers, which facilitate the penetration of the active agent and preferably dissolve the active ingredient present in the formulations of the invention.

In certain embodiments, the topical gel formulation comprises

| Category of ingredient |
| --- |
| Active (Montelukast or a salt thereof) |
| Water miscible organic solvent |
| Penetration enhancer |
| Antioxidant |
| Chelating Agent |
| Water |
| Preservative |
| Gelling agent |

The gel formulation may also comprise pH adjusting agents and occlusive agents. The concentration of above category of ingredient/ingredients may be determined based on knowledge by the person skill in the art.

Examples of Specific Gel Formulation Include:
(a) Formula 1

| Category | Ingredient | % W/W |
| --- | --- | --- |
| Active | Montelukast sodium | 5.00 |
| Water miscible organic solvent | Alcohol 96% | 25.00 |
| Penetration enhancer | DMSO | 10.00 |
| Antioxidant | BHT | 0.10 |
| Chelating Agent | EDTA | 0.10 |
| Water | Purified water | 57.90 |
| Preservative | Methyl paraben | 0.30 |
| Preservative | Propyl paraben | 0.10 |
| Gelling agent | Hydroxyethylcellulose ($M_w$ 90,000 to 1,300,000) | 1.50 |
| pH adjusting agent | HCl (10% solution) | q.s. | b) Formula 2

| Category of ingredient | Ingredient | % W/W |
|---|---|---|
| Occlusive ingredient | Dimethicone | 1 |
| Occlusive ingredient | Cyclomethicone | 4 |
| Active | Montelukast sodium | 3 |
| Emulsifier | Silicone Glycerol emulsifier | 1.5 |
| Occlusive ingredient | Cetearyl Ethylhexanoate | 2.5 |
| Water miscible organic solvent | Glycerin | 3.0 |
| Solvent | Water | Up to 100 |
| Gelling agent | Sodium Carbomer | 2.5 |
| Lubricant | Sodium Hyaluronate | 1.0 | c) Formula 3

| Ingredient | % W/W |
|---|---|
| Montelukast sodium | 1% |
| Alcohol | 25% |
| BHT | 0.10% |
| Purified water | 60.00 |
| DMSO | 10.00% |
| Methyl paraben | 0.30% |
| Propyl paraben | 0.10% |
| Carbopol 947P (polymers of acrylic acid) | 0.40% |
| EDTA | 0.10% |
| Sepineo 600 (Acrylamide/Sodium Acryloyldimethyl Taurate copolymer/isohexadecane and Polysorbate 80 | 3% | d) Formula 4

| Category of ingredient | Ingredient | % W/W |
|---|---|---|
| Active | Montelukast sodium | 1% |
| Water miscible organic solvent | Alcohol | 25% |
| Antioxidant | BHT | 0.10% |
| Water | Purified water | 60.00 |
| Penetration enhancer | DMSO | 10.00% |
| Preservative | Methyl paraben | 0.30% |
| Preservative | Propyl paraben | 0.10% |
| Gelling agent | Carbopol 947P (polymers of acrylic acid) | 0.40% |
| Chelating agent | EDTA | 0.10% |
| Emulsifier/Thickener/Stabilizer | Sepineo 600 (Acrylamide/Sodium Acryloyldimethyl Taurate copolymer/ isohexadecane and Polysorbate 80 | 3% |
| pH adjusting agent | Citric acid buffer | To pH 5.6 | e) Formula 5

| Category of ingredient | Ingredient | % W/W |
|---|---|---|
| Active | Montelukast sodium | 1% |
| Water miscible organic solvent | Alcohol | 25% |
| Antioxidant | BHT | 0.10% |
| Water | Purified water | 60.00 |
| Penetration enhancer | DMSO | 10.00% |
| Preservative | Methyl paraben | 0.30% |
| Preservative | Propyl paraben | 0.10% |
| Gelling agent | Carbopol 947P (polymers of acrylic acid) | 0.40% |
| Chelating agent | EDTA | 0.10% |
| Emulsifier/Thickener/Stabilizer | Sepineo 600 (Acrylamide/Sodium Acryloyldimethyl Taurate copolymer/ isohexadecane and Polysorbate 80 | 3% |
| pH adjusting agent | Phosphate Buffer | pH 5.6 |

In one embodiment, the present invention relates to a topical formulation comprising Montelukast or a pharmaceutically acceptable salt thereof, at least one oil for the treatment of atopic dermatitis wherein the formulation is waterless.

In one embodiment of the present invention, the waterless topical formulation comprising Montelukast or a pharmaceutically acceptable salt may further a topically acceptable solvent and an amphiphilic compound.

In another embodiment, the waterless formulation may be an ointment. In another embodiment, the waterless formulation may be a solution. In another embodiment, the waterless formulation may be a gel. The waterless formulations may include a variety of additional components such as, but not limited to solvents, emulsifiers, chelating agents, surfactants, emollients, permeation enhancers, preservatives, antioxidants, lubricants, pH adjusters.

In one embodiment, the ointment may comprise an amphiphilic compound. The examples of suitable amphiphilic compounds include, but are not limited to vegetable oils, animal fats, and semisolid hydrocarbons obtained from petroleum.

In one embodiment, examples of amphiphilic compound include polypropylene glycol −15 stearyl ether, propylene glycol monostearate (monosteol), Poloxylhydrogenated Castor oil, oleyl alcohol, polyoxyglycerides, propylene carbonate Examples of oils, such as poloxylhydrogenated castor oil (e.g. trihydroxystearin), fractionated coconut oil, or olive oil; an occlusive ingredient, such as petroleum jelly/white petrolatum, a wax, an oil, a silicone, glycerin; an MCT of e.g. hexanoic acid, octanoic acid, decanoic acid or dodecanoic acid; lubricants such as Cyclomethicone and Dimethicone 5225C, Cyclomethicone, polypropylene glycol −15 stearyl ether; an antioxidant, such as butylated hydroxy anisole or butylated hydroxyl toluene; or any combination thereof.

In certain embodiments, the topical formulation may comprise an occlusive ingredient selected from the group of siloxanes such as cyclomethicone, dimethicones; petroleum jelly/white petrolatum.

In one aspect of the invention, the topical formulation of montelukast or a pharmaceutically acceptable salt may comprise a triglyceride. In a preferred embodiment, if a triglyceride is present, it may be a medium chain triglyceride (MCT) of e.g. hexanoic acid; octanoic acid; decanoic acid or dodecanoic acid.

In certain embodiments, the topical waterless formulation comprises:

| Category of ingredient |
|---|
| Active (Montelukast or a salt thereof) |
| Water miscible organic solvent |
| Amphiphilic compound |
| Occlusive ingredient |
| Oil |
| Antioxidant |

The gel formulation may further comprise a gelling agent.

The concentration of above category of ingredient/ingredients may be determined based on knowledge by the person skill in the art.

In one embodiment, the waterless formulation of montelukast or a pharmaceutically acceptable salt can be:

a solution comprising

| Category of Ingredient | Ingredient | % W/W |
|---|---|---|
| Topically acceptable solvent | Alcohol (Dehydrated) | 34.5 |
| Amphiphilic compound | Poloxylhydrogenated Castor | 2.5 |
| Active | Montelukast sodium | 3 |
| oil | Fractionated Coconut oil | 60 | or a gel formulation comprising

| Category of ingredient | Ingredient | % W/W |
|---|---|---|
| Topically acceptable solvent | Alcohol (Dehydrated) | 31 |
| Amphiphilic compound | Poloxylhydrogenated Castor | 2.5 |
| Active | Montelukast sodium | 3 |
| oil | Fractionated Coconut oil | 60 |
| Gelling agent | Hydroxy propyl cellulose | 3.5 | or an ointment comprising

| Category of ingredient | Ingredient | % W/W |
|---|---|---|
| Active | Montelukast sodium | 0.5-5 |
| Occlusive ingredient | Petroleum jelly/white petrolatum | 80 |
| Oil | Trihydroxystearin | 1-3 |
| oil | Olive oil | 12-18.5 | or an ointment comprising

| Category of ingredient | Ingredient | % W/W' |
|---|---|---|
| Active | Montelukast sodium | 0.5-5 |
| Water miscible organic solvent | Glycerine | 65-75 |
| Oil | Medium chain triglycerides | 20 |
| Antioxidant | Antioxidant | 0-0.5 | or an ointment comprising

| Category of ingredient | Ingredient | % W/W' |
|---|---|---|
| Active | Montelukast Sodium | 5 |
| Antioxidant | BHT | 0.08 |
| Occlusive ingredient | Cyclomethicone | 94.52 |
| Amphiphilic compound | Cyclomethicone and Dimethicone | 0.40 | or an ointment comprising

| Category of ingredient | Ingredient | % W/W' |
|---|---|---|
| Active | Montelukast Sodium | 5 |
| Antioxidant | BHT | 0.08 |
| Occlusive ingredient | Petrolatum White | 55.92 |
| Amphiphilic compound | PPG-15 Stearyl Ether | 16 |
| Oil | Medium Chain Triglycerides | 20 |
| Amphiphilic compound | Monosteol | 3 |

API is milled to <5 micron size. Homogenous distribution of crystals ointment was observed or an ointment comprising

| Category of ingredient | Ingredient | % W/W' |
|---|---|---|
| Active | Montelukast Sodium | 5 |
| Antioxidant | BHT | 0.08 |
| Occlusive ingredient/ | Petrolatum White | 49.92 |
| Oil | Mineral Oil | 45 |

In certain embodiments, each one of the topical formulations described above further comprises an additional active agent, such as an anti-pruritic agent, such as pramoxine; an antihistamine; an anti-inflammatory agent, such as a corticosteroid (e.g. hydrocortisone or desoximetasone), or a glucocorticosteroid; an antibacterial agent, such as dapson (diaminodiphenyl sulfone) or minocycline; a vitamin, such as vitamin B, C, D or E; a non-steroidal anti-inflammatory drug (NSAID); a peripheral analgesic agent; or a different leukotriene receptor antagonist, such as zafirlukast or pranlukast, or a pharmaceutically acceptable derivative thereof.

In another aspect, the present invention provides a topical formulation comprising a pharmaceutically acceptable carrier and a microparticle(s) or nanoparticle(s) comprising an active agent selected from the group consisting of a leukotriene receptor antagonist, such as an antagonist specific to cysLT1, and a pharmaceutically acceptable derivative thereof.

The active agent may be montelukast, zafirlukast or pranlukast, or a pharmaceutically acceptable derivative thereof. In certain embodiments the active agent is montelukast, e.g. montelukast sodium. The microparticles or nanoparticles of this topical formulation may be as defined above.

In certain embodiments, each one of the topical formulations described above is formulated as a gel, solution, suspension, lotion, paste, cream, ointment, aerosol, dusting powder or a patch.

In an additional aspect, the present invention provides a topical formulation for use in the treatment of atopic dermatitis, wherein said topical formulation is any one of the topical formulations defined herein above.

In a further aspect, the present invention is directed to a method for the treatment of atopic dermatitis in a patient in need thereof, comprising administering to the patient any one of the topical formulations defined herein above.

In certain embodiments, the use or method comprises topically exposing the patient to said formulation once or twice daily; for example, the use or method comprises exposing the patient to a formulation that comprises about 0.5% to about 5% montelukast sodium.

In case the topical formulation comprises microparticles or nanoparticles encapsulating the active agent, they provide targeting of the active agent to hair follicles.

In certain embodiments, the topical formulation described above comprises a formulation selected from the group consisting of:

(a) a solid lipid nanoparticle (SLN) dispersion comprising

| Ingredient | % W/W |
|---|---|
| Montelukast sodium | 2.0 |
| Emulsifiers (e.g. Poloxamer188/polysorbate 20) | 0.75 |

-continued

| Ingredient | % W/W |
|---|---|
| Lipids/Hard fat/Triglycerides (e.g, Compritol, Cocoa butter, Phosphatidylcholine) | 15 |
| Water | Up to 100 |

(b) a liposomal formulation comprising Sphingomyelin/cholesterol e.g. in the molar ratio of 2:1; phosphatidyl choline/cholesterol e.g. in the molar ratio of 3:1; phosphatidyl ethanolamine/phosphatidyl choline/cholesterol e.g. in the molar ratio of 3:4:2 as representative examples; and (c) a formulation of polymeric nanocapsules based on a polymer selected from the group consisting of a silicone; poly(lactic-co-glycolic acid (PLGA); polylactic acid (PLA); chitosan; gelatine; ethylcellulose; polycaprolactone; a polyalkyl cyanoacrylate and any combination thereof.

In certain embodiments, in the topical formulation comprising encapsulating nanoparticles, the particles have a size (diameter) of up to about 1000 nm.

EXAMPLES

Example 1

Montelukast in a Gel Formulation

| Category | Ingredient | % W/W |
|---|---|---|
| Active | Montelukast sodium | 5.00 |
| Water miscible organic solvent | Alcohol 96% | 25.00 |
| Penetration enhancer | DMSO | 10.00 |
| Antioxidant | BHT | 0.10 |
| Chelating Agent | EDTA | 0.10 |
| Water | Purified water | 57.90 |
| Preservative | Methyl paraben | 0.30 |
| Preservative | Propyl paraben | 0.10 |
| Gelling agent | Hydroxyethylcellulose ($M_w$ 90,000 to 1,300,000) | 1.50 |
| pH adjusting agent | HCl (10% solution) | q.s. |

Example 2

Montelukast in a Gel Formulation

| Category of ingredient | Ingredient | % W/W |
|---|---|---|
| Occlusive ingredient | Dimethicone | 1 |
| Occlusive ingredient | Cyclomethicone | 4 |
| Active | Montelukast sodium | 3 |
| Emulsifier | Silicone Glycerol emulsifier | 1.5 |
| Occlusive ingredient | Cetearyl Ethylhexanoate | 2.5 |
| Water miscible organic solvent | Glycerin | 3.0 |
| Solvent | Water | Up to 100 |
| Gelling agent | Sodium Carbomer | 2.5 |
| Lubricant | Sodium Hyaluronate | 1.0 |

Example 3

Montelukast in a Gel Formulation

| Category of ingredient | Ingredient | % W/W |
|---|---|---|
| Active | Montelukast sodium | 1% |
| Water miscible organic solvent | Alcohol | 25% |
| Antioxidant | BHT | 0.10% |
| Water | Purified water | 60.00 |
| Penetration enhancer | DMSO | 10.00% |
| Preservative | Methyl paraben | 0.30% |
| Preservative | Propyl paraben | 0.10% |
| Gelling agent | Carbopol 947P (polymers of acrylic acid) | 0.40% |
| Chelating agent | EDTA | 0.10% |
| Emulsifier/Thickener/Stabilizer | Sepineo 600 (Acrylamide/Sodium Acryloyldimethyl Taurate copolymer/isohexadecane and Polysorbate 80 | 3% | pH was adjusted to 5.6 with citric/phosphate buffer

Example 4

Montelukast in a Gel Formulation

| Category of ingredient | Ingredient | % W/W |
|---|---|---|
| Active | Montelukast sodium | 5% |
| Water miscible organic solvent | Alcohol | 22.4% |
| Antioxidant | BHT | 0.10% |
| Water | Purified water | 56.00 |
| Penetration enhancer | DMSO | 10.00% |
| Preservative | Methyl paraben | 0.30% |
| Preservative | Propyl paraben | 0.10% |
| Gelling agent | Carbopol 947P (polymers of acrylic acid) | 0.40% |
| Chelating agent | EDTA | 0.10% |
| Emulsifier/Thickener/Stabilizer | Sepineo 600 (Acrylamide/Sodium Acryloyldimethyl Taurate copolymer/isohexadecane and Polysorbate 80 | 3% |

Crystals of montelukast are present in the formula

Example 5

Montelukast in a Gel Formulation

| Category of ingredient | Ingredient | % W/W |
|---|---|---|
| Active | Montelukast sodium | 3% |
| Water miscible organic solvent | Alcohol | 22.4% |
| Antioxidant | BHT | 0.10% |
| Water | Purified water | 57.5% |
| Penetration enhancer | DMSO | 10.00% |
| Preservative | Methyl paraben | 0.30% |
| Preservative | Propyl paraben | 0.10% |
| Gelling agent | Carbopol 947P (polymers of acrylic acid) | 1.5% |
| Chelating agent | EDTA | 0.10% |
| Emulsifier/Thickener/Stabilizer | Sepineo 600 (Acrylamide/Sodium Acryloyldimethyl Taurate copolymer/isohexadecane and Polysorbate 80 | 3% |
| pH adjusting agent | Phosphate buffer or citrate buffer | pH adjusted to 5.6 |

Crystals of montelukast are present in the formula

To protect montelukast from light and increase its stability particulate drug carriers can be formulated (e.g. oil in water or water in oil emulsions, liposomes, microparticles and nanoparticles of polymers (synthetic or natural), solid lipid nanoparticles in which sodium montelukast is encapsulated (dissolved or suspended))

Waterless formulations in which sodium montelukast can be dissolved or suspended are another route for preparation of stable formulations. Typically the waterless formulations contain at least one oil.

Example 6

Non Aqueous Solution Formulation (Waterless Formulation)

| Category of Ingredient | Ingredient | % W/W |
|---|---|---|
| Topically acceptable | Alcohol (Dehydrated) | 34.5 |
| Amphiphilic compound | Poloxylhydrogenated Castor | 2.5 |
| Active | Montelukast sodium | 3 |
| oil | Fractionated Coconut oil | 1 |

Example 7

Ointment (Waterless Formulation)

| Category of ingredient | Ingredient | % W/W |
|---|---|---|
| Active | Montelukast sodium | 0.5-5 |
| Occlusive ingredient | Petroleum jelly/white petrolatum | 80 |
| Oil | Trihydroxystearin | 1-3 |
| oil | Olive oil | 12-18.5 |

Example 8

Ointment (Waterless Formulation)

| Category of ingredient | Ingredient | % W/W |
|---|---|---|
| Active | Montelukast sodium | 0.5-5 |
| Water miscible organic solvent | Glycerine | 65-75 |
| Oil | Medium chain triglycerides | 20 |
| Antioxidant | Antioxidant | 0-0.5 |

Example 9

Ointment (Waterless Formulation)

| Category of ingredient | Ingredient | % W/W |
|---|---|---|
| Active | Montelukast Sodium | 5 |
| Antioxidant | BHT | 0.08 |
| Occlusive ingredient | Petrolatum White | 55.92 |
| Amphiphilic compound | PPG-15 Stearyl Ether | 16 |
| Oil | Medium Chain Triglycerides | 20 |
| Amphiphilic compound | Monosteol | 3 |

Example 10

Ointment (Waterless Formulation)

| Category of ingredient | Ingredient | % W/W |
|---|---|---|
| Active | Montelukast Sodium | 5 |
| Antioxidant | BHT | 0.08 |
| Occlusive ingredient/ | Petrolatum White | 49.92 |
| Oil | Mineral Oil | 45 |

Crystals of less than 5 micron are homogenously dispersed in the ointment formulation Example 11

Colloidal Particle Formulation/SLN (Solid Lipid Nanoparticle) Dispersion

| Ingredient | % W/W |
|---|---|
| Montelukast sodium | 2.0 |
| Emulsifiers (Poloxamer188/polysorbate 20) | 0.75 |
| Lipids/Hard fat/Triglicerides (Comprilol, Cocoa butter, Phosphatidylcholine) | 15 |
| Water | Up to 100 |

Colloidal Gel Formulation of Polymeric Nanocapsules

Various techniques can be used to produce polymer nanoparticles in which montelukast would be encapsulated, such as solvent evaporation, salting-out, dialysis, supercritical fluid technology, micro-emulsion, nano-emulsion, surfactant-free emulsion, and interfacial polymerization. The choice of method depends on a number of factors, such as, particle size, particle size distribution, area of application, etc.

The produced polymeric nanoparticles would be suspended in a cream or a gel formulation. Typical polymers that are in use for the production of pharmaceutical nanoparticles are silicon, PLGA, PLA, chitosan, gelatine, ethylcellulose, polycaprolactone and poly alkyl cyanoacrylates.

Example 12

Lipid Nano Emulsion

| Ingredient | % W/W |
|---|---|
| Soybean oil | 10-7.0 |
| Lecithin | 1 |
| Glycerol | 2 |
| Montelukast | 1 |
| Water | Up to 100 |

Example 13

Solution Formulation (Substantially Anhydrous)

| Ingredient | % W/W |
|---|---|
| Montemkast sodium | 5% |
| Alcohol (96%) | 66.45 |
| BHT | 0.1% |
| Propylene glycol | 28.45 |

Example 14

Montelukast in a Cream Formulation

| Ingredient | % W/W |
|---|---|
| Montelukast sodium | 5% |
| Propylene glycol | 10% |
| DMSO | 10% |
| Methylparaben | 0.3% |
| Propylparaben | 0.1% |
| BHT | 0.1% |
| MCT | 10% |
| Glyceryl Stearate & PEG-100 Stearate | 5% |
| Purified water | 59.1% |
| Natrosol 250 HEC HHX | 0.30% |
| EDTA | 0.1% |
| HCl (10% sol) | q.s. |

Crystals of montelukast are present in the formula

Example 15

Animal Model of Atopic Dermatitis with Repeated DNCB Patch in BALB/c Mice

The following is the animal model which is being used to test the efficacy of the formulation of the present invention for atopic dermatitis. Repeated 2,4-dinitrochlorobenzene, (DNCB) applications is a common animal model of AD which possesses benefits of reproducibility.

Montelukast sodium topical gel (Example 1, RD#14152) and Montelukast sodium topical cream (Example 14, RD#14153) formulations for the treatment of Atopic dermatitis (Efficacy studies).

Balb/c mice were used for the study. The animals were sensitized on Day 1 by application of 100 μl of 1% DNCB in acetone:olive oil (Figaro) 3:1 on shaved dorsal back skin and 10 μl of 1% DNCB on right ear from day 1 to day 4. On day 6, animals were weighed using digital weighing balance. After 4 hr of treatment, animals were challenged by application of 100 μl of 0.5% DNCB in acetone:olive oil (3:1) on dorsal back skin and 20 μL of 0.5% DNCB on right ear on day 8, day 10, day 12, day 14. Normal control animals were sensitized and challenged with acetone and olive oil alone. 200 mg of Montelukast sodium topical gel and Montelukast sodium topical cream were topically applied in around 5-6 cm$^2$ area on the back skin of the mice for 9 days from day 6 to day 14. Respective placebo items were topically applied in around 5-6 cm$^2$ area on the back skin of the mice for 9 days from day 6 to day 14. Bethametasone valerate cream was used as the reference item 0.40 mg of reference item was applied topically per animal on the back skin for 9 days from day 6 to day 14. All the vials of test items were opened and test items were topically applied under yellow sodium lamp light. The animals were kept under yellow sodium lamp light up to 4 hours after application.

In one embodiment of the present invention, clinical scoring has been performed to determine the efficacy of tested formulations with appropriate controls as a part of the study. On day 15, back skin severity scores were assessed as following criteria 1) Erythema (0-3), 2) Excoriation/Erosion (0-3), 3) Scarring/Dryness in each symptoms was scored by following criteria no lesion, 0; mild, 1; moderate, 2; severe, 3. Total maximum cumulative score was 9 as defined as the sum of these individual scores.

TABLE 1

Erythema (0-3), Excoriation/Erosion 0-3), Scaring/Dryness (0-3) and Total Cumulative Score (0-9) after Montelukast Topical Cream (Example 14, RD # 14153) or Gel (Example 1, RD # 14152) Treatment (from day 6 to 14) in DNCB-induced Atopic Dermatitis in Balb/c Mice on day 15, n = 10

| Group No | Dose Groups | Erythema | Excoriation/Erosion | Scarring/Dryness | Total cumulative score |
|---|---|---|---|---|---|
| | | MEAN ± SEM | | | |
| 1 | Normal Control | 0.00 ± 0.00 | 0.00 ± 0.00 | 0.00 ± 0.00 | 0.00 ± 0.00 |
| 2 | Disease Control | 2.70 ± 0.21*** | 1.60 ± 0.27*** | 1.70 ± 0.15*** | 6.00 ± 0.45*** |
| 3 | Placebo of Montelukast Sodium gel of Example 1 | 2.40 ± 0.16 | 1.60 ± 0.27 | 1.90 ± 0.10 | 5.90 ± 0.43 |
| 4 | Montelukast sodium gel of Example 1 | 2.10 ± 0.18 | 0.80 ± 0.25$ | 1.70 ± 0.15 | 4.60 ± 0.43$ |
| 5 | Placebo of Montelukast Sodium cream of Example 14 | 2.20 ± 0.25 | 1.20 ± 0.20 | 1.90 ± .10 | 5.30 ± 0.30 |
| 6 | Montelukast sodium cream of Example 14 | 2.40 ± 0.16 | 1.40 ± 0.27 | 2.20 ± 0.20 | 6.00 ± 0.45 |
| 7 | Betamethasone valerate cream IP | 1.20 ± 0.20#### | 1.20 ± 0.25 | 1.70 ± 0.15 | 4.10 ± 0.28#### |

Data were analyzed by 2-tailed Student's t-test
Normal Control vs Disease control group (* = p < 0.05,  = p < 0.01, * = p < 0.001)
Disease control group vs Betamethasone Valerate cream (# = p < 0.05, ## = p < 0.01, ### = p < 0.001)
Placebo of Montelukast Sodium gel vs Monlelukast Sodium gel ($ = p < 0.05, $$ = p < 0.01, $$$ = p < 0.001)
Placebo of Montelukast Sodium cream vs Montelukasl Sodium cream (@ = p < 0.05, @@ = p < 0.01, @@@ = p < 0.001).

Data were analyzed by 2-tailed Student's t-test
Normal Control vs Disease control group (*=p<0.05, =p<0.01, *=p<0.001)
Disease control group vs Betamethasone Valerate cream (#=p<0.05, ##=p<0.01, ###=p<0.001)
Placebo of Montelukast Sodium gel vs Montelukast Sodium gel ($=p<0.05, $$=p<0.01, $$$=p<0.001)
Placebo of Montelukast Sodium cream vs Montelukast Sodium cream (@=p<0.05, @@=p<0.01, @@@=p<0.001).

As seen in Table 1, there was a significant increase in erythema, excoriation, dryness and total cumulative score in disease control group (DNCB) as compared to the normal control group. Montelukast sodium topical gel showed significant inhibition in excoriation as compared to its placebo. Also, the excoriation/erosion score of Montelukast sodium topical gel was lower than that of the Betamethasone valerate cream indicating that the gel reduced the excoriation or the erosion more than the Bethametasone valerate cream. A significant inhibition in the total cumulative score of Montelukast sodium topical gel was seen as compared to its placebo. Betamethasone valerate cream showed significant inhibition in erythema and total cumulative score but did not show significant inhibition in excoriation as compared to the disease control group.

Figure 1:
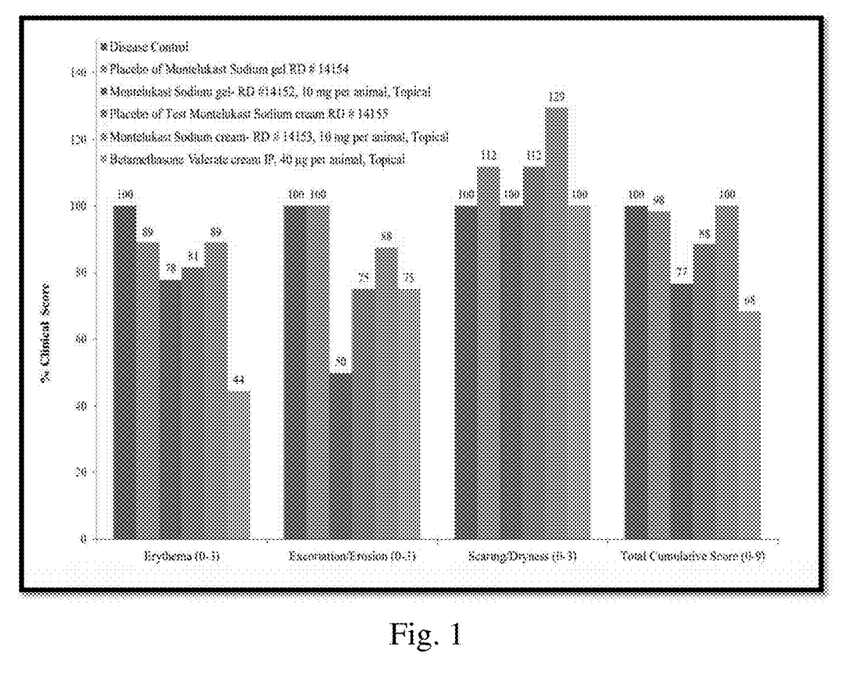
FIG. 1 describes the % Clinical Score (Erythema, Excoriation/Erosion, Scaring/Dryness and Total Cumulative) compared to Disease Control after Montelukast Topical Gel (Example 1) (RD#14152) Treatment (from day 6 to 14) in DNCB-induced Atopic Dermatitis in Balb/c Mice on day 15, n=10
Figure 2A:
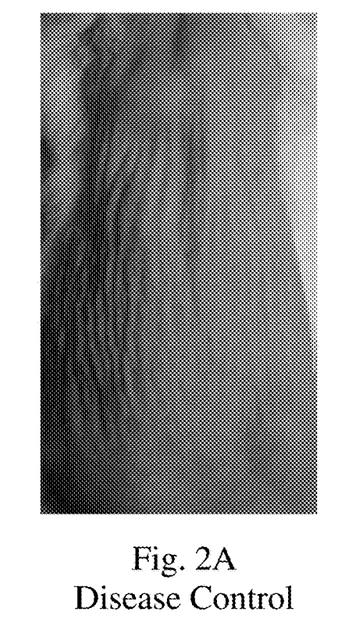
FIG. 2A-2G—Photographs (representative) of Animal's Back Skin after Montelukast Topical cream (Example 14) and Montelukast Topical Gel Treatment (Example 1) (from day 6 to 14) in DNCB-induced Atopic Dermatitis in Balb/c Mice on day 15, n=10
Figure 2B:
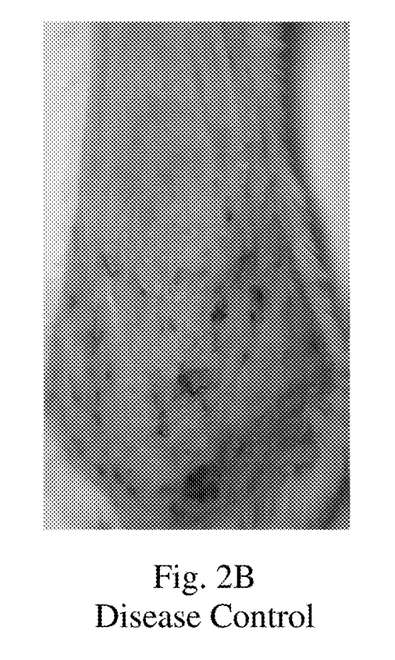
Figure 2C:
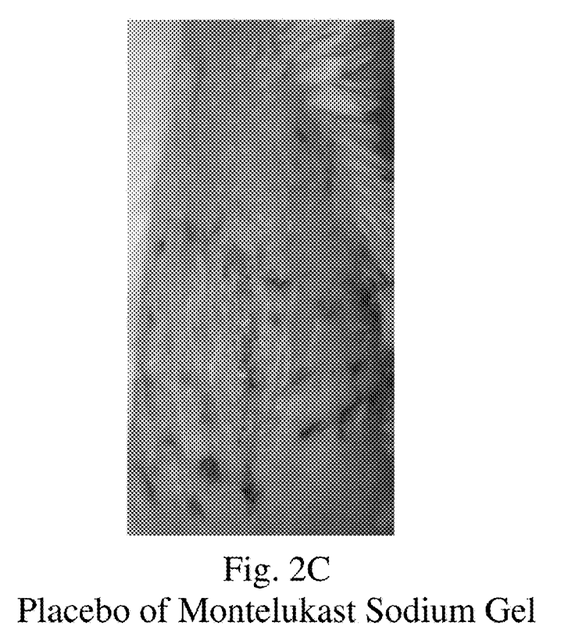
Figure 2D:
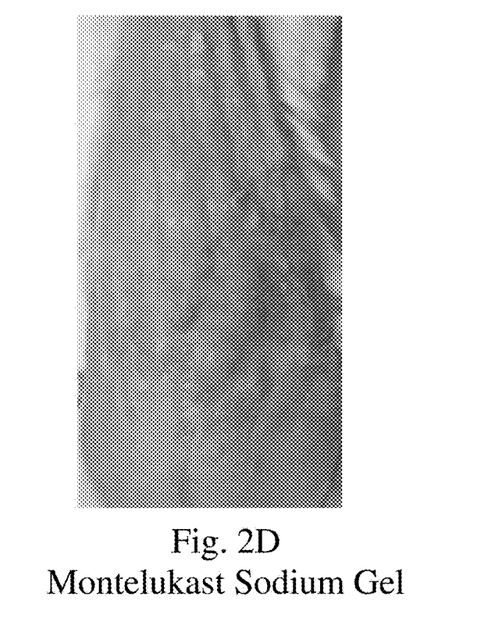
Figure 2E:
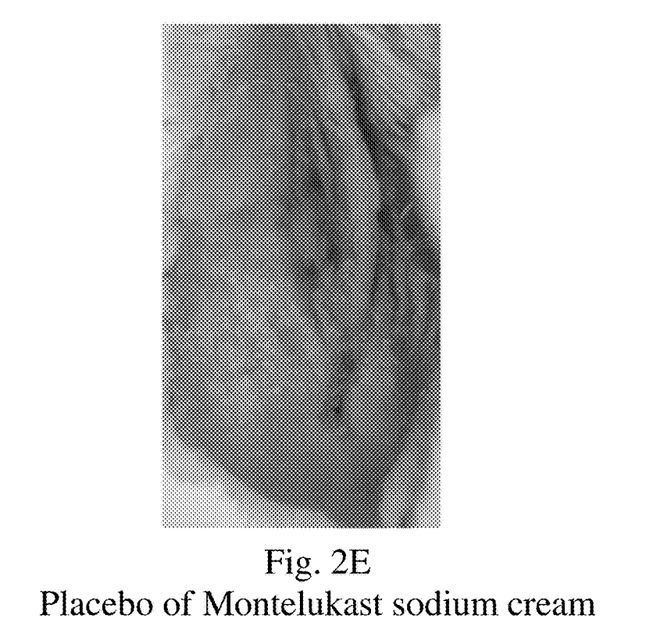
Figure 2F:
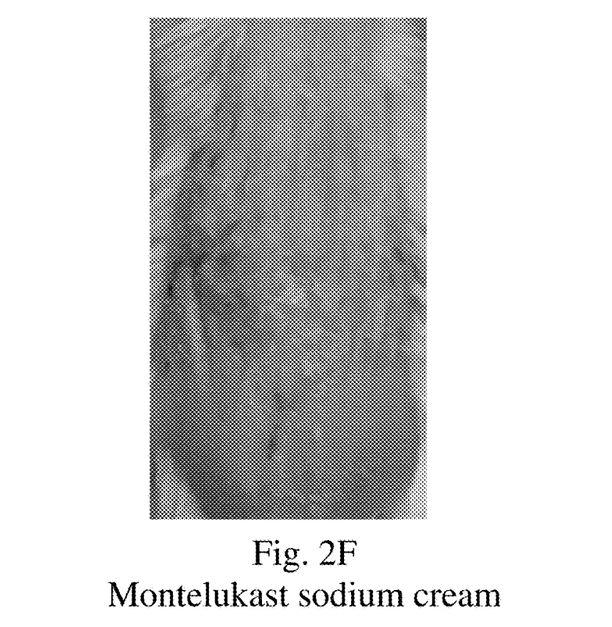
Figure 2G:
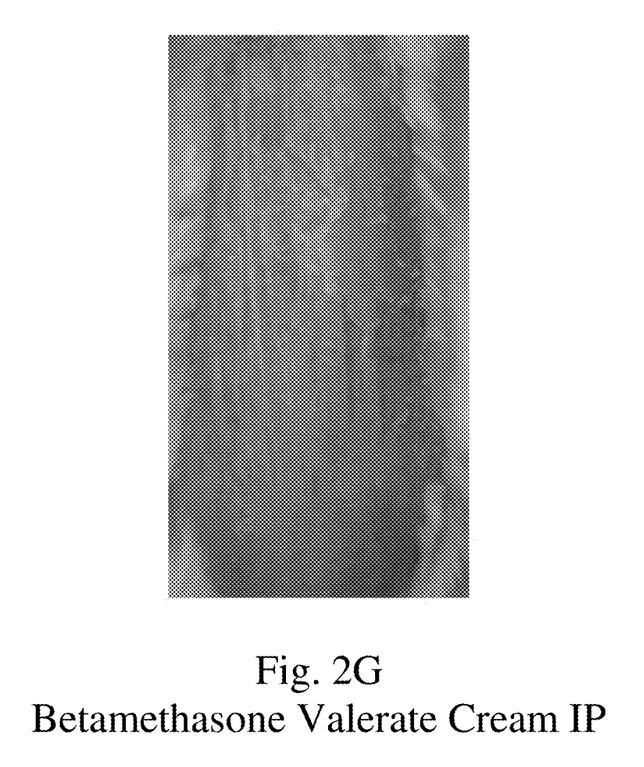

In one embodiment of the present invention, the % clinical score (Erythema, Excoriation/erosion, Scarring/dryness and Total cumulative) of the disease control group, the placebo groups, Montelukast sodium topical cream group and the Montelukast sodium topical gel group were compared. (FIG. 1). As seen in FIG. 1, the % clinical score of Montelukast sodium topical gel for erythema was lower i.e 78% as compared to the disease control which showed a score of 100%. The % clinical score of the gel for erythema was also lower as compared to its placebo. Bethametasone valerate cream showed a % clinical score of 100% which was lower among all the treatment groups. Montelukast sodium topical gel group showed 50% clinical score for excoriation/erosion as compared to its placebo, the disease control, the montelukast sodium topical cream group and its placebo and the Bethametasone valerate cream group. The total cumulative score of the group treated with Montelukast sodium topical gel was 77% as compared to the disease control and the placebo group. Montelukast sodium topical gel was effective for erythema as compared to the placebo and the disease control groups. (FIG. 2)

In one embodiment of the present invention, DNCB induced atopic dermatitis of the skin in mice reproduces biochemical and histopathological parameter characteristic of atopic dermatitis in humans.

Tissue collection—The animals were sacrificed by $CO_2$ asphyxiation. The back skin was collected and was preserved in 50 ml falcon tube containing 10% formalin for histologic analysis or was stored in micro centrifuge tube at $-70°$ C. for cytokine analysis.

Cytokine estimation—For determination of cytokines levels, the skin samples were removed from $-70°$ C. and kept on ice. The 20% w/v tissue homogenate was prepared by adding cocktail protease inhibitor to the tubes containing weighed skin tissues. The skin tissue homogenate was prepared in 5 ml cryovials using a homogenizer under constant cooling using an ice bath. Each skin tissue was homogenized for 30-90 seconds with approximately 19000 to 26000 rpm. After every run, the homogenizer probe was washed first with 70% v/v isopropyl alcohol followed by PBS (pH 7.4). The probe was then wiped with a dry tissue paper before the next run. Homogenized samples were centrifuged at 10,000 rpm for 10 min at 4'C. The resulting supernatant was separated in micro centrifuge tube and snap frozen in liquid nitrogen and stored in $-70°$ C. Cytokines like IL-4, TNF-$\alpha$ and IFN-$\Upsilon$ were estimated in skin homogenate supernatant using mouse ELISA kits (R&D systems). Cytokine levels were normalized to the amount of total proteins as determined by Bicinchoninic acid assay.

TABLE 2

Levels of Cytokines (IL-4 TNF-$\alpha$ and IFN-$\gamma$) ng/gm of Protein in Back Skin Homogenate after Montelukast Topical Cream and Montelukast Topical Gel Treatment (from day 6 to 14) in DNCB-induced Atopic Dermatitis in Balb/c Mice on day 15, n = 10

| Group | | Ng/gm of protein in back skin homogenate (MEAN ± SD) | | |
|---|---|---|---|---|
| No | Dose Groups | IL-4 | TNF-$\alpha$ | IFN-$\gamma$ |
| 1 | Normal Control | 0.00 ± 0.00 | 0.00 ± 0.00 | 0.00 ± 0.00 |
| 2 | Disease Control | 19.14 ± 7.67*** | 8.28 ± 3.36*** | 1.40 ± 0.58** |
| 3 | Placebo of Montelukast Sodium topical gel of Example 1 | 17.79 ± 9.25 | 6.68 ± 4.34 | 1.74 ± 0.27 |
| 4 | Montelukast sodium topical gel of Example 1 | 18.99 ± 6.64 | 4.37 ± 1.94 | 1.29 ± 0.31$$ |
| 5 | Placebo of Montelukast Sodium cream of Example 14 | 16.82 ± 3.80 | 5.28 ± 3.49 | 1.75 ± 0.74 |
| 6 | Montelukast sodium topical cream of Example 14 | 18.20 ± 9.72 | 4.42 ± 3.62 | 1.67 ± 0.68 |
| 7 | Betamethasone valerate cream IP | 3.06 ± 1.35### | 4.96 ± 4.53 | 0.71 ± 0.26## |

Data were analyzed by 2-tailed Student's t-test
Normal Control vs Disease control group (* = p < 0.05,  = p < 0.01, * = p < 0.001)
Disease control group vs Betamethasone Valerate cream (# = p < 0.05, ## = p < 0.01, ### = p < 0.001)
Placebo of Montelukast Sodium gel vs Monlelukast Sodium gel ($ = p < 0.05, $$ = p < 0.01, $$$ = p < 0.001)
Placebo of Montelukast Sodium cream vs Montelukasl Sodium cream (@ = p < 0.05, @@ = p < 0.01, @@@ = p < 0.001)

Data were analyzed by 2-tailed Student's t-test
Normal Control vs Disease control group (*=p<0.05, =p<0.01, *=p<0.001)
Disease control group vs Betamethasone Valerate cream (#=p<0.05, ##=p<0.01, ###=p<0.001)
Placebo of Montelukast Sodium gel vs Montelukast Sodium gel ($=p<0.05, $$=p<0.01, $$$=p<0.001)
Placebo of Montelukast Sodium cream vs Montelukast Sodium cream (@=p<0.05, @@=p<0.01, @@@=p<0.001)

Figure 3:
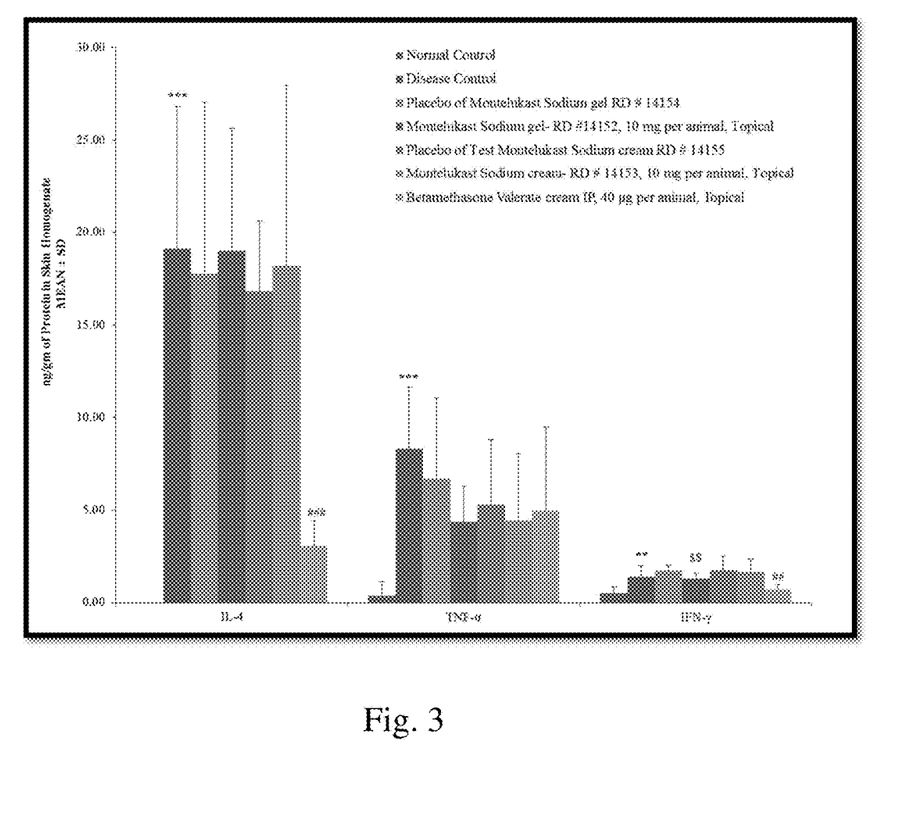
FIG. 3 describes the Levels of Cytokines (IL-4, TNF-α and IFN-ϒ) ng/gm of Protein in Back Skin Homogenate after Montelukast Topical Cream (Example 14, RD#14153) and Montelukast Topical Gel (Example 1, RD#14152) Treatment (from day 6 to 14) in DNCB-induced Atopic Dermatitis in Balb/c Mice on day 15, n=10

As seen in Table 2, the topical application of dinitrochloro benzene increased the levels of cytokines such as IL-4, TNF-$\alpha$ and IFN-$\gamma$ in the disease control group as compared to the normal control group. Montelukast sodium topical gel showed significant inhibition in IFN-$\gamma$ levels in skin homogenate as compared to its placebo. Betamethasone Cream showed significant inhibition in IL-4 and IFN-$\Upsilon$ levels in skin homogenate but did not show significant inhibition in TNF-α level as compared to disease control group. (FIG. 3)

Immunohistochemistry (Ki67) Evaluation—

Images were captured from hematoxylin and eosin (H and E) stained skin sections at a magnification of 100× using ZEISS AxioA1 microscope. The unstained sections were processed for immunohistochemistry of Ki67 marker using Ki67 Immunohistochemistry Kit (Eton Bioscience, Inc). The images were captured using ZEISS AxioA1 microscope at 100× magnification.

Figure 4:
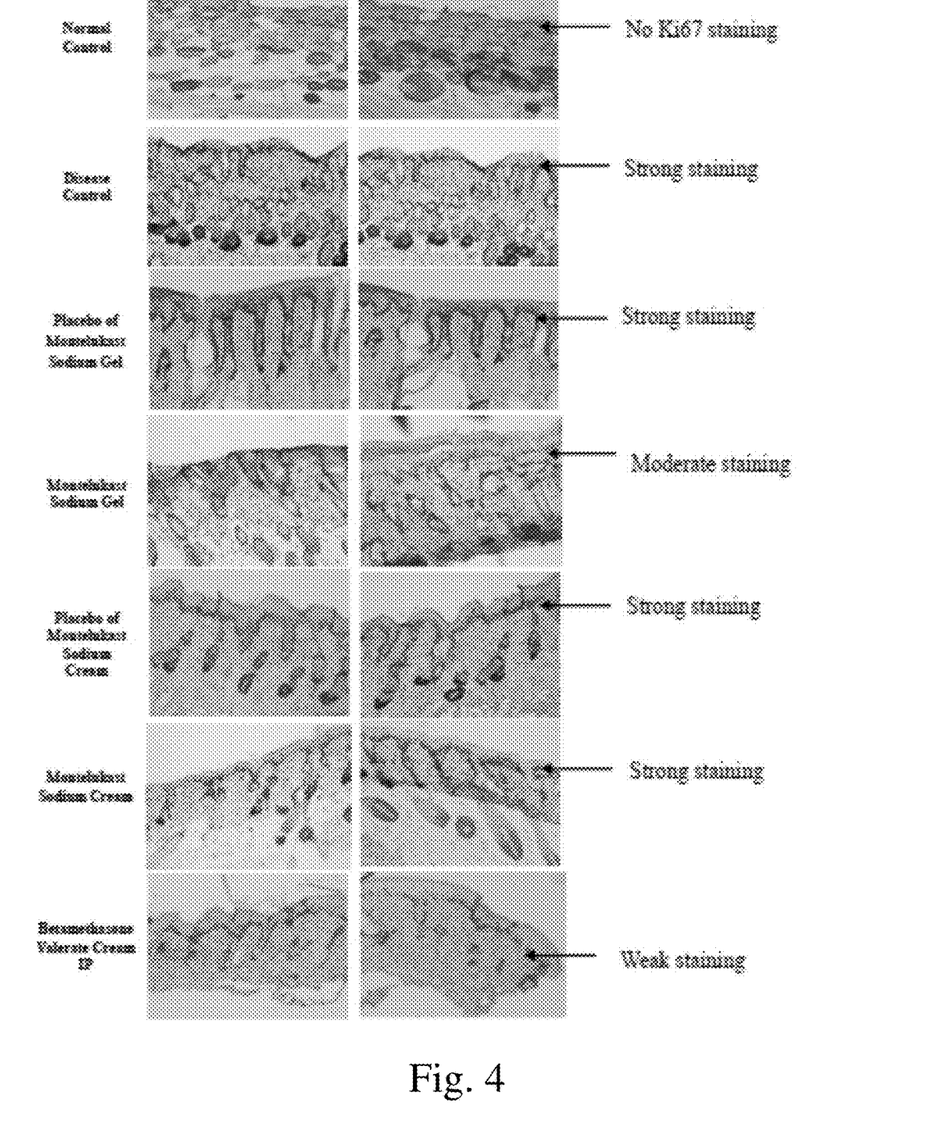
FIG. 4—Images (representative) of Ki67 Immunohistochemistry of Back Skin section at 100× magnification after Montelukast Topical Cream (Example 14, RD #14153) and Montelukast Topical Gel (Example 1, RD#14152) Treatment (from day 6 to 14) in DNCB-induced Atopic Dermatitis in Balb/c Mice on day 15, n=10

The Ki67 is a cellular marker for proliferation and is associated with cell proliferation. The immunohistochemistry in FIG. 4 demonstrates strong Ki67 staining in the back skin sections of disease control groups as compared to the normal control groups. Weak Ki67 staining was observed in the group treated with Betamethasone valerate cream as compared to the disease control group. Placebos of Montelukast sodium topical gel and Montelukast sodium topical cream showed strong staining of Ki67 comparable to the disease control group. However, Montelukast sodium gel showed moderate Ki67 staining as compared to its placebo. Also, it also showed moderate staining as compared to the disease control group. Thus, cell proliferation was less pronounced in the group treated with Montelukast sodium topical gel as compared to its placebo and the disease control group.

Example 16

In Vitro Skin Permeation Studies

The in vitro skin permeation studies were determined using vertical static Franz cells. Two pieces of excised heat-separated human skin were used in this study. A total of 10 cells were used for each formulation with an average application of 14.07±2.5 mg/cm$^2$, 4.5 ml receptor solution was used in this study. The receptor solution was a mixture 30% Ethanol in Phosphate buffer saline. The receptor solution was sampled at 6 time points in addition to $t_0$. After 24 hours, the skin surface was washed using pre-developed washing procedure), the skin surface was then tape stripped (≤10 time). Both, the tape strips and skin were extracted with 3 ml and 2 ml in 80% ethanol in water, respectively, for 24 hours under agitation. Wash, tape, skin and permeation samples were analyzed to determined mass balance. Total recoveries only were corrected for the assay.

Results indicated that more than 80% of the applied formulations were recovered on the skin surface. Formulation Montelukast sodium gel (example 1) and substantially anhydrous topical solution (example 13) showed higher depositions in the stratum corneum (SC) and skin compared to the cream formulation (example 14). Specifically, between about 0.5% to about 1% of Montelukast was deposited within the skin including the SC in the gel formulation and the anhydrous solution.

The safety, tolerability, pharmacokinetics and bioavailability of topical montelukast are assessed according to methods well known in the art, for example according to Cheng H, Leff J A, Amin R, Gertz B J, De Smet M, Noonan N, Rogers J D, Malbecq W, Meisner D, Somers G. Pharmacokinetics, bioavailability, and safety of montelukast sodium (MK-0476) in healthy males and females. Pharm Res. 1996 March; 13(3):445-8.

Example 17

Combination Product:

Montelukast is combined with anti-pruritic/anti histamines/anti-inflammatory/anti-bacterial agents/vitamines (e.g pramoxine, hydrocortisone, desoximetasone, dapsone, minocycline vitamin E/B/C/D etc.) and tested as described above.

The invention claimed is:

1. A method of treating atopic dermatitis, comprising the step of:
    administering a homogeneous topical formulation comprising Montelukast or a pharmaceutically acceptable salt thereof and at least one gelling agent selected from the group consisting of hyaluronic acid and a salt thereof, a cellulose derivative, a carbomer, and a polymer of acrylic acid, to a patient in need,
        wherein the concentration of Montelukast is from about 0.5% weight/weight to about 10% weight/weight.

2. The method of claim 1, wherein Montelukast is essentially suspended or is solubilized in the formulation.

3. The method of claim 1, wherein the concentration of Montelukast or a pharmaceutically acceptable salt is between about 5% w/w to about 10% w/w.

4. The method of claim 1, wherein between about 0.5% to about 1% of Montelukast is deposited within the skin following topical application.

5. The method of claim 1, wherein the formulation further comprises a water miscible organic solvent.

6. The method of claim 1, wherein the formulation further comprises a penetration enhancer.

7. The method of claim 1, wherein the formulation further comprises a preservative.

* * * * *